(12) United States Patent
Koshiji (10) Patent No.: US 7,359,483 B2
(45) Date of Patent: Apr. 15, 2008

(54) RADIOGRAPHER SUPPORT SYSTEM

(75) Inventor: Fukuro Koshiji, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 703 days.

(21) Appl. No.: 10/966,061

(22) Filed: Oct. 18, 2004

(65) Prior Publication Data

US 2005/0097220 A1   May 5, 2005

(30) Foreign Application Priority Data

Oct. 21, 2003   (JP) .............................. 2003-360483

(51) Int. Cl.
*H05G 1/56* (2006.01)
(52) U.S. Cl. ..................... 378/116; 378/98.8
(58) Field of Classification Search ................ 378/116, 378/189–191, 98.8, 210; 250/370.09; 340/573.1
See application file for complete search history.

(56) References Cited

U.S. PATENT DOCUMENTS

| | | | |
|---|---|---|---|
| 5,773,839 A | 6/1998 | Krepel et al. | |
| 5,811,897 A * | 9/1998 | Spaude et al. | 307/149 |
| 6,315,719 B1 * | 11/2001 | Rode et al. | 600/300 |
| 6,344,652 B1 | 2/2002 | Shoji | |
| 6,805,484 B2 * | 10/2004 | Kuramoto et al. | 378/189 |
| 2004/0140898 A1 * | 7/2004 | Reeves | 340/573.1 |
| 2006/0252371 A1 * | 11/2006 | Yanagida | 455/41.1 |

FOREIGN PATENT DOCUMENTS

EP   1 413 921 A1   4/2004

OTHER PUBLICATIONS

European Search Report for EP 04 25 6406, issued on Jan. 13, 2005.

* cited by examiner

*Primary Examiner*—Hoon Song
(74) *Attorney, Agent, or Firm*—Finnegan, Henderson, Farabow, Garrett & Dunner, L.L.P.

(57) ABSTRACT

A radiographer support system containing a storage apparatus provided in a case including a recoding medium for recording radiographic image data a recording device for recording radiograph related data of the first radiographic image data a first communication device electrically connected to the recording device for a data communication and a first electrode electrically connected to the first communication device capable of being in contact with a human body, and a wearable apparatus including a second communication device for communicating with the first communication device and a second electrode electrically connected to the second communication device capable of being in contact with a human body wherein the first communication device communicate with the second communication device for transmitting the radiographic image data or X-ray photograph related data each other via a human body as a transmission line.

25 Claims, 10 Drawing Sheets

RADIOGRAPHER SUPPORT SYSTEM

BACKGROUND

The present invention relates to a radiographer support system for supporting a radiographer taking radiographs.

Conventionally, in a medical field, the digitalization of medical images of a patient has been established and medical image apparatuses such as CR (Computer Radiography), a FPD (Flat Panel Detector), etc. has been utilized.

CR is a phosphor plate using a supporting body on which a stimulable phosphor layer is formed. After having radiographic rays transmit a patient body, irradiating excited rays to the phosphor plate, and then the radiographic energy absorbed in the phosphor plate is excited. And the phosphor plate emits fluorescent lights. Image signals are obtained by converting the emitting beams of the fluorescent lights via a photoelectric converter. The phosphor plate is stored in a cassette being transportable and a reader dedicated for the cassette can read the images.

It is necessary for a radiographer to know the name of patient being a radiographic object, and a part being radiographed, etc. For example, a barcode label on which the patient name and the name of radiographic object are coded is attached on the cassette beforehand. And the barcode is read to identify and confirm the patient name and the the part being radiographed. In any case, in order to know the information of the patient name and the radiographic part, it is necessary for a radiographer to move to the place where a barcode reading apparatus or a barcode reader is placed. It takes time to confirm them and it becomes a cause of the delay of a work.

As an alternative communication method, it is possible to transfer data using a radio as a radio LAN (Local Area Network) and an infrared communication. However, data leakages occur and a security level goes down since electromagnetic waves spreads around.

Consequently, A more easier and safer method for transmitting information is expected. For example, proposed is a method for transmitting information from a transmitter being in contact with a human body to a receiver via a human body. (Refer to Patent Reference 1)

(Patent Reference 1) Japanese Patent Open to Public Inspection No. 2003-37566.

However, there is no description about a communication method using a human body as a transmission line applied for a cassette used for a radiograph in the patent reference.

SUMMARY

A present invention proposes a radiographer support system capable of obtaining radiographic image data or radiograph related data from a storage apparatus storing radiographic images of a patient to solve the problems described above to provide.

EMBODIMENT 1

In accordance with one aspect of a present invention provided is a radiographer support system containing
a storage apparatus provided in a case including:
a recoding medium for recording radiographic image data;
a recording device for recording radiograph related data of the first radiographic image data;
a first communication device electrically connected to the recording device for a data communication; and
a first electrode electrically connected to the first communication device capable of being in contact with a human body, and
a wearable apparatus including:
a second communication device for communicating with the first communication device; and
a second electrode electrically connected to the second communication device capable of being in contact with a human body; wherein
the first communication device communicate with the second communication device for transmitting the radiographic image data or X-ray photograph related data each other via a human body as a transmission line.

EMBODIMENT 2

In accordance with another aspect of a present invention provide is the radiographer support system of EMBODIMENT 1, wherein the Radiograph related data includes one at least of a name of patient to be radiographed, a name of a portion to be radiographed, a name of radiographer or a date when radiographed.

EMBODIMENT 3

In accordance with another aspect of a present invention provide is the radiographer support system of EMBODIENT 1 or 2, wherein the wearable apparatus includes a display device for displaying the radiographic image data or the radiograph related data, or a voice outputting device for outputting the radiograph related data in a voice.

EMBODIMENT 4

In accordance with another aspect of a present invention provide is the radiographer support system of EMBODIMENT 3, wherein the wearable apparatus displays or outputs that the storage apparatus is unused for a radiograph in an image or in a voice when the storage apparatus is unused.

EMBODIMENT 5

In accordance with another aspect of a present invention provide is the radiographer support system as in any one of EMBODIMENTS 1-4, wherein the wearable apparatus communicates with another wearable apparatus being put on a human body of the same human being via the human body as a transmission line.

EMBODIMENT 6

In accordance with another aspect of a present invention provide is the radiographer support system as in any one of EMBODIMENTS 1-5, wherein
the storage apparatus further comprising a power receiving antenna for receiving power and
the wearable apparatus further comprising a power transmitting antenna for transmitting power to the receiving antenna, wherein
the wearable apparatus transmits power needed for data communication to the storage apparatus either via a human body or an air space as a transmission line.

EMBODIMENT 7

In accordance with another aspect of a present invention provide is the radiographer support system as in any one of EMBODIMENTS 1-24, wherein the wearable apparatus is designed in a shape of a wristwatch, a head-mounted display, a headphone or PDA (Personal Digital Assistance).

According to the EMBODIMENT 1, since data communication is established between the first electrode and the second electrode via a human body as a transmission line, the wearable apparatus can receive a radiographic image data or radiographic related data of the radiographic image data from the storage apparatus. Accordingly, the radiographer can easily check the radiographic image data or the radiograph related data.

According to the EMBODIMENT 2, the radiographer can easily check the name of a name of patient to be radiographed, a name of a portion to be radiographed, a name of radiographer or a radiographing date since the radiograph related data contains the name of patient to be radiographed, the name of a portion to be radiographed, the name of radiographer or the date when radiographed.

According to the EMBODIMENT 3, the radiographic image data and the radiograph related data can be provided to a radiographer in characters, an image and a voice since the wearable apparatus can display the radiographic image data or output the radiographic related data in characters or in a voice.

According to the EMBODIMENT 4, a wearable apparatus can display and output that the storage apparatus is unused for a radiograph in a image or in a voice when the storage apparatus is unused.

According to the EMBODIMENT 5, plural wearable apparatuses can share data since a wearable apparatus communicates with another wearable apparatus being put on a human body of the same human being via the human body as a transmission line.

According to the EMBODIMENT 6, a portable storage apparatus does not need to have a power supply for supplying necessary power for communication since a wearable apparatus transmits power needed for data communication to the storage apparatus either via a human body or an air space as a transmission line.

According to the EMBODIMENT 7, a radiographer can obtain radiographic image data and radiograph related data via a wristwatch, a head-mounted display, a headphone or PDA configured to being in contact with a human body.

DESCRIPTION OF THE PREFERRED EMBODIMENT

The example of the present invention will be described below. However, the scope of the present invention is no limited to this example.

EXAMPLE 1

Figure 1:
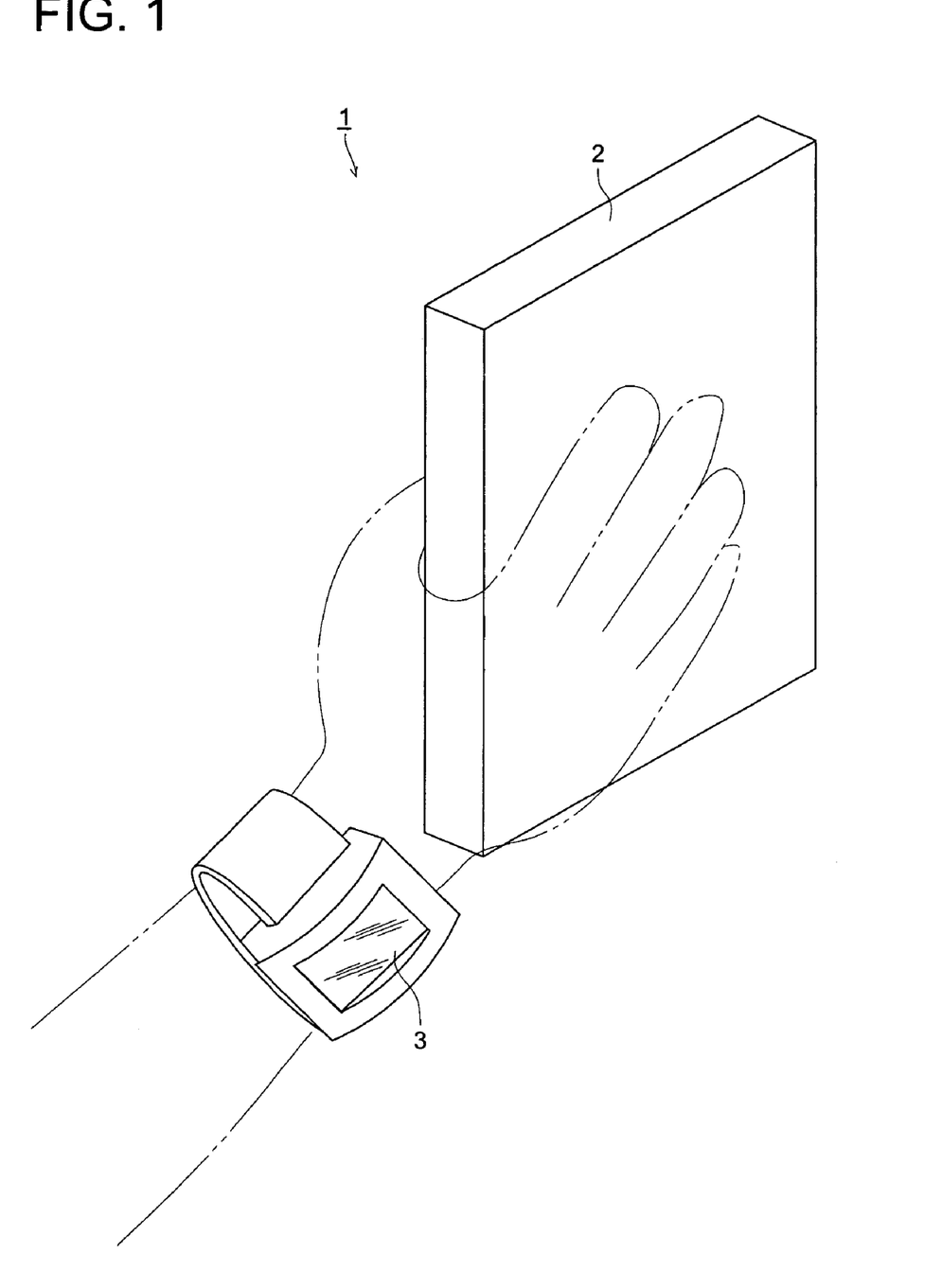
FIG. 1 is the block diagram of a X-ray radiograph support system 1 of EXAMPLE 1.

EXAMPLE 1 will be explained by using FIGS. 1-10. FIG. 1 shows the appearance of radiographer support system. As shown in FIG. 1, radiographer support system 1 comprises a cassette type flat panel detector 2 (cassette type FPD 2) and wearable apparatus 3. Cassette type FPD 2 communicates with wearable apparatus 3 via a human body as a transmission line. Wearable apparatus 3 is an apparatus capable of being wearable on a human body. In this example, wearable apparatus 3 of a wrist watch type (a belt wearable type) is used as an example and will be described. Wearable apparatus may have a watch function therewith.

Figure 2:
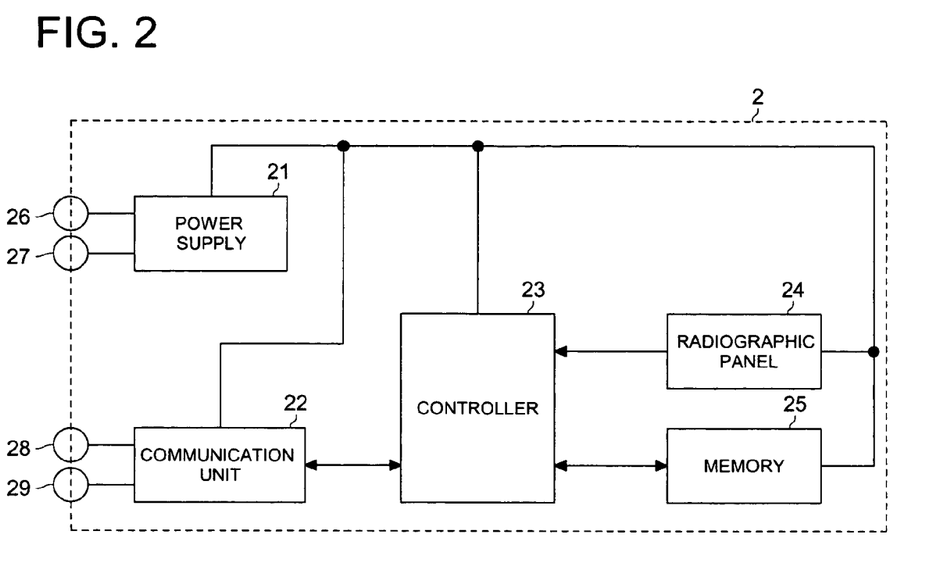
FIG. 2 is a block diagram showing the functional configuration of cassette type FPD 2.

The functional block diagram of cassette type FPD2 is shown in FIG. 2. As shown in FIG. 2, Cassette type FPD 2 comprises power supply 21, communication device 22, controller 23, imaging panel 24, memory 25, charging terminal 26, power receiving antenna 27, electrode 28 and PC communication terminal 29 are provided in a case so that cassette type FPD 2 can be transportable.

Power supply 21 comprises a battery or rechargeable battery and supplies power to each portion in cassette type FPD 2. Power supply 21 can be charged via charging terminal 26. Power can be supplied via power receiving terminal 27 while cassette type FPD 2 communicates with wearable apparatus 3.

Communication device 22 comprises a transmitter for sending data and a receiver for receiving data to communicate with wearable apparatus 3 via a human body as a transmission line and a communication apparatus for communicating with PC (personal computer), etc. Communication with PC, etc. is conducted when reading out a radiographic image data from cassette type FPD 2 by using PC, etc. and to input radiograph related data to cassette type FPD2.

Controller 23 comprises CPU (Central Processing Unit, not shown), ROM (Read Only Memory) etc, and controls communication device 22, imaging panel 24 and memory 25. CPU executes various processes working under various programs stored in ROM according to inputted data from communication device 24.

Imaging panel 24 comprises a phosphor layer having phosphor as a main ingredient which emits lights corresponding to a quantity of irradiated X-rays, a charge generating layer for converting an electromagnetic wave emitted from the phosphor layer into electric energy and switching elements for outputting accumulated electric energy, and generates a radiographic image data. Memory 25 stores he radiographic image data.

Memory 25 comprises volatile memory such as SRAM (Static Random Access Memory) or SDRAM (Synchronous Dynamic Random Access Memory), etc. or a non-volatile memory such as flash memory, etc. Memory 25 stores radiograph related data of a radiograph and radiographic image data generated by imaging panel 24. Memory 25 is also used when controller 24 needs to temporarily store data. The radiograph related data is information such as the name of a patient being radiographed, a portion to be radiographed, a name of a radiographer and a radiographing date, etc.

Charging terminal 26 is not only an interface for charging power supply 21 but also a connector to a cradle. The cradle is a stand type connecting apparatus by which cassette type FPD 2 can communicate with PC, etc. by putting thereon.

Power receiving antenna 27 is an interface for receiving power from wearable apparatus 27 and is provided on the surface or the interior of cassette type FPD 2. Data sending/receiving to/from wearable apparatus 3 is conducted under power supplied from wearable apparatus.

Electrode 28 is provided on the surface of the case and is electrically connected to the transmitter and the receiver of communication device 22. Electrode 28 is an interface to send and to receive data to and from wearable apparatus 3 via a human body as a transmission line. Electrode 28 is provided on the side surface, etc. of the case, which is the outside of a radiographing area of cassette type FPD 2 and data communication is conducted by being touched by a radiographer.

Terminal for PC 29 is not only for an interface communicating with PC, etc. being connected with the cassette type FPD but also a connector to a cradle. PC communication terminal 29 is connected to a communication apparatus communicating with PC of communication device 22.

Figure 3:
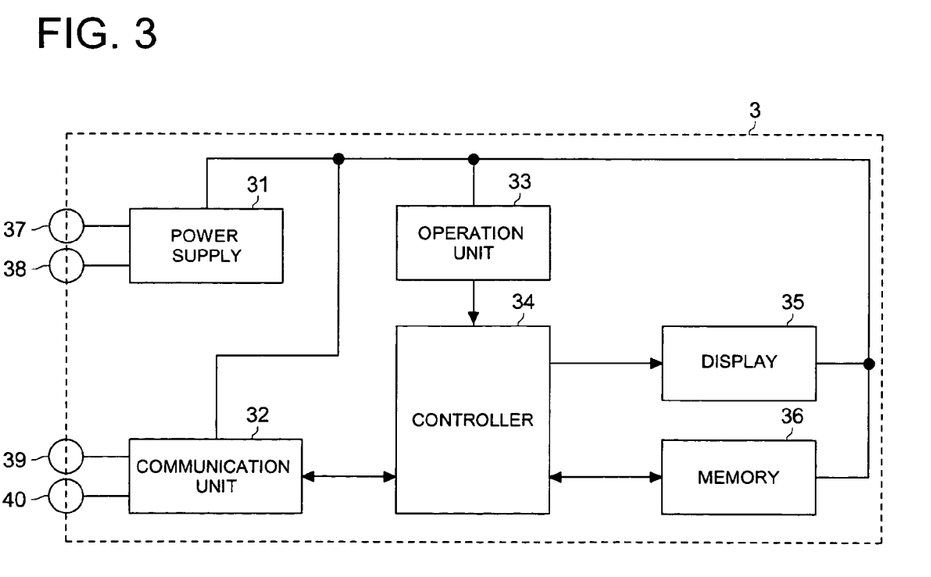
FIG. 3 is a block diagram showing the functional configuration of wearable apparatus 3.

The functional configuration of wearable apparatus 3 will be described below. As shown in FIG. 3, wearable apparatus 3 contains power supply 32, communication device 32, operation unit 33, controller 34, display device 35, memory 36, charging terminal 37, power transmitting antenna 28, electrode 39 and PC communication terminal 40.

Power supply 31 comprises a battery or a rechargeable battery and supplies power to each functional block of wearable apparatus 3. Power supply 31 is charged though charging terminal 37 provide on the surface of wearable apparatus 3.

Communication device 32 comprises a transmitter and a receiver communicating with cassette type FPD 2 or other wearable apparatuses for sending/receiving data via a human body as a transmission line.

Operation unit 33 contains various function buttons outputting a signal to controller 34 when correspond button is pushed down. These buttons are used for changing display contents displayed on display 35, resetting the display contents and forcibly communicating with other apparatus.

Controller 34 comprises CPU (not shown) and ROM, etc. and controls communication device 32, operation unit 33, display 35 and memory 36. CPU executes various processes working with various programs stored on ROM according to the direction inputted from communication device 32 or operation unit 33.

Display 35 comprises flat panel displays such as LCD (Liquid Crystal Display) or organic EL (Electro Luminescence), etc. for displaying data received from cassette type FPD 2 or a wearable apparatus.

Memory 36 comprises volatile memory such as SRAM or SDRAM, etc. or non-volatile memory such as flash memory, etc. Memory 36 stores data received from cassette type FPD2 or wearable apparatus.

Charging terminal 37 is an interface for charging power supply 31.

Power transmitting antenna 38 is an interface for transmitting power to cassette type FPD 2, which is provided on the inside or on the outside surface of wearable apparatus 3.

Electrode 39 electrically connected to the transmitter and the receiver of communication device 32 is provided on the surface of wearable apparatus 3. Electrode 39 is an interface for data exchange between cassette type FPD 2 or other wearable apparatus using a human body as a transmission line.

PC communication terminal 40 is an interface being connected with PC, etc. for communication with PC.

Figure 4:
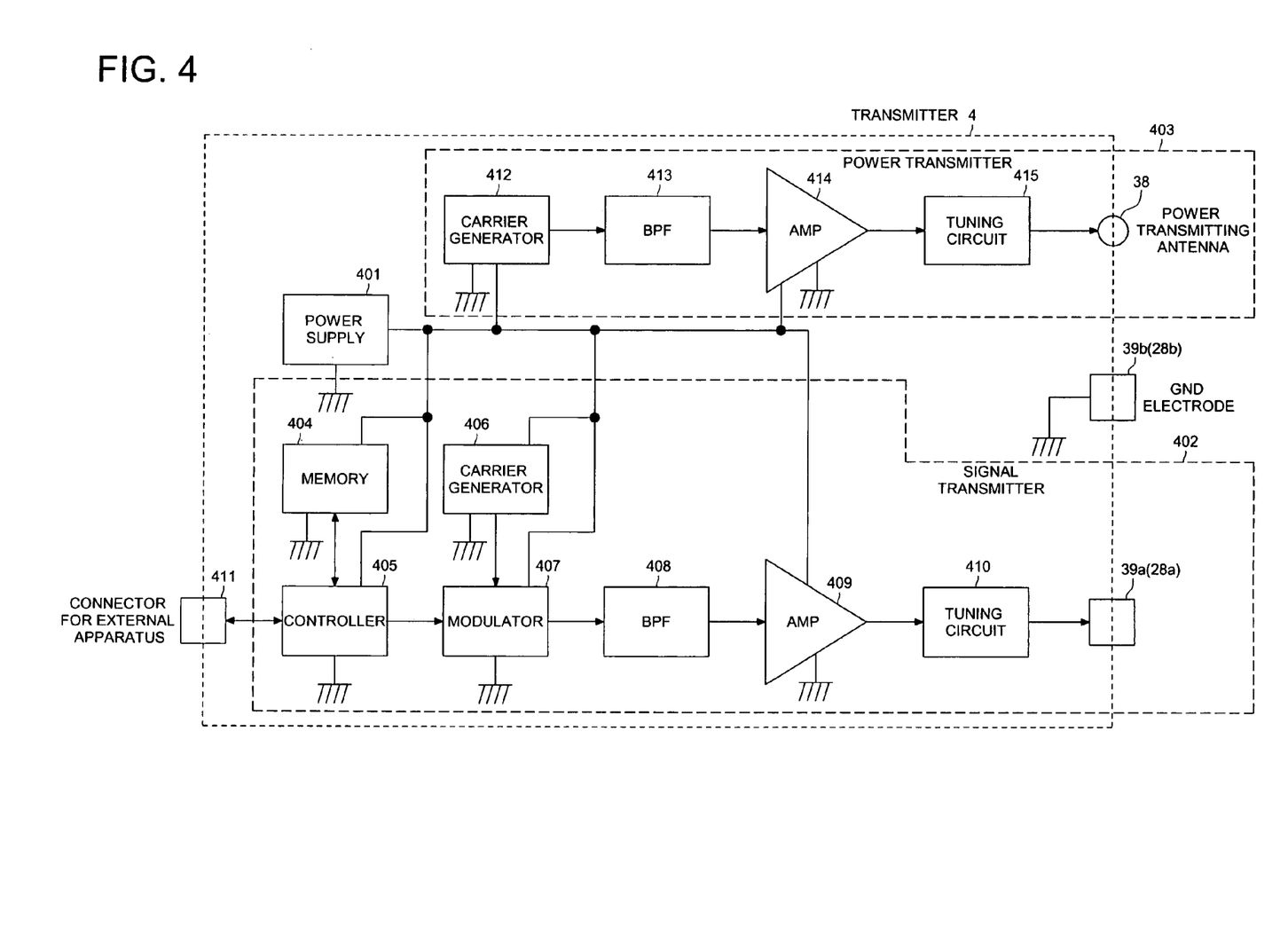
FIG. 4 is a block diagram showing the functional configuration of transmitter 4.
Figure 5:
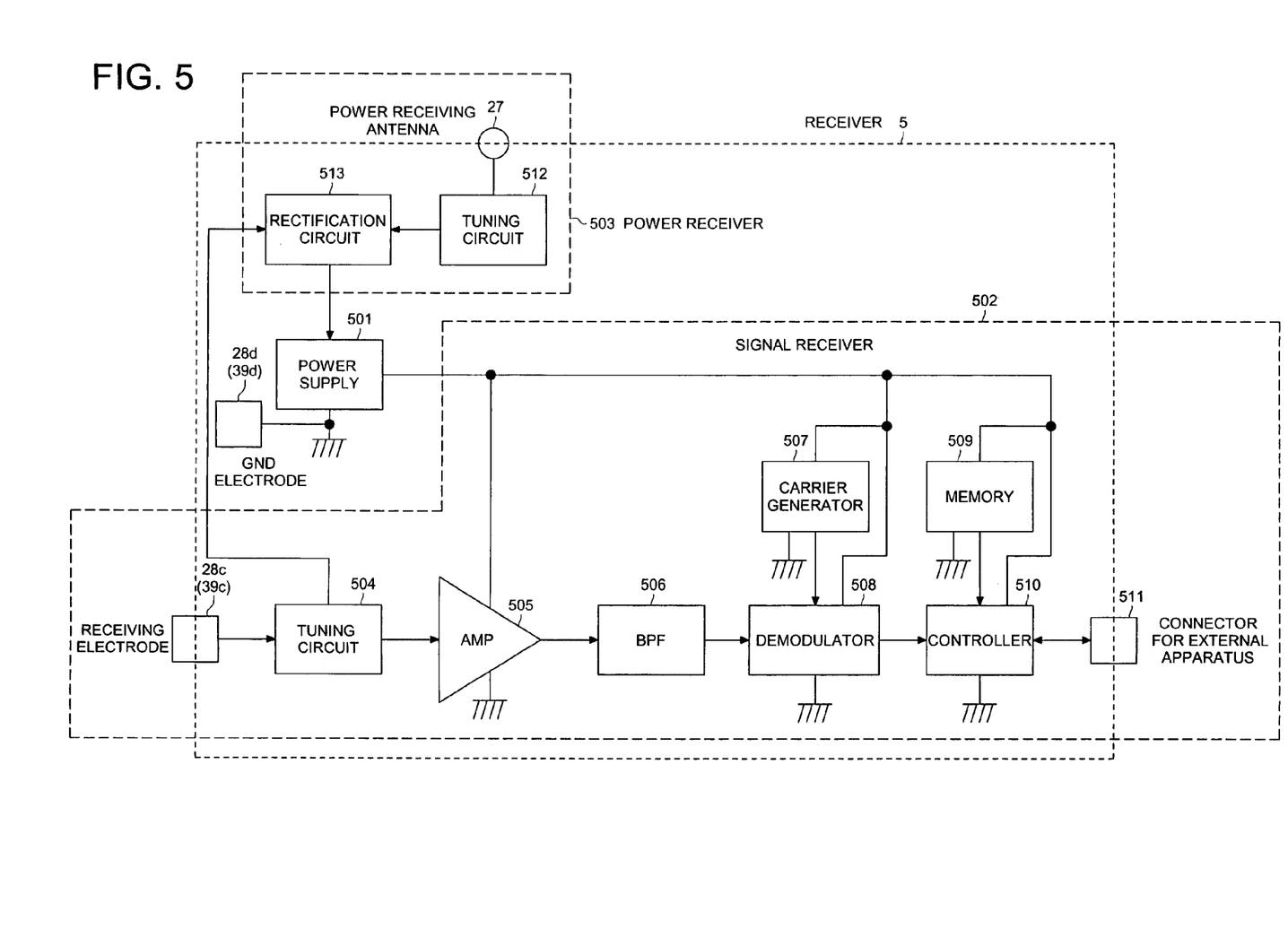
FIG. 5 is a block diagram showing the functional configuration of receiver 5.

Next, transmitter 4 and receiver 5, which are included in the communication device 22 of cassette type FPD 2 and communication device 32 in wearable apparatus 32 will be described below.

Firstly, the functional configuration of transmitter 4 in wearable apparatus 3 will be described. As shown in FIG. 4, transmitter 4 contains power supply 401, signal transmitter 402 including power transmission function and power transmitter 403, etc.

Power supply 401 comprises battery or rechargeable battery supplying power to each unit. Power supply 31 in wearable apparatus 3 can replaces power supply 401.

Signal transmitter 402 contains memory 404, controller 405, carrier generator 406, modulator 407, band-pass filter 408 (BPF will be used from now on), amplifier 409 (AMP will be used from now on) and tuning circuit 410.

Memory 404 usually works as a memory, which temporarily stores data from internal transmitter 4 of wearable apparatus 3 via connector 411 which is a connector for outside equipment. The memory comprises a volatile memory such as SRAM or SDRAM, etc. or non-volatile memory such as flash memory, etc. Memory 36 in wearable apparatus 3 may replace memory 404.

Controller 405 usually comprises CPU, etc. and controls transmitter 4. Controller 405 processes data stored in memory 404 or data inputted via connector 411 and outputs data to modulator 407. Controller 34 in wearable apparatus may replace controller 405.

Carrier generator 406 generates carrier to transmit data.

Modulator 407 modulates carrier according to data from controller 405 and outputs modulated signal to BPF 408.

BPF 408 removes noise signals (higher harmonic waves) being generated in modulator 407 from modulated signals inputted from modulator 407, purifies it into a predetermined frequency signal and outputs to AMP 409.

AMP 409 amplifies the modulated signal and outputs tuning circuit 410.

Tuning circuit 410 comprises a resonance circuit which functions as a filter circuit for outputting a signal having a needed frequency from signals amplified by AMP 409. And also tuning circuit 410 has an effect on matching the impedance of tuning circuit 410 to the impedance of a human body as a transmission line and effectively outputs the signal. The output terminal of tuning circuit 410 is connected to transmission electrode 39a of wearable apparatus 3.

Transmission electrode 39a and GND electrode 39b (electrode 39 in FIG. 3) are provided so that both electrodes are in contact with a human body respectively. Since in data communications via a human body as a transmission line, an electric signal transmits on the surface of a skin, the shape of GND electrode 39b may be a shape of an antenna. Grounding GND electrode 39b may not be necessary. However providing GND electrode 39b can effectively transmits the signal.

Power transmitter 403 contains carrier generator 412, BPF 413, AMP 414 and tuning circuit 415. Since a signal outputted from power transmitter 403 is to supply power to cassette type FPD 2, the superposition of data signal is not conducted. It is defined that the frequency of a data signal transmitted from transmission electrode 39a and that of a signal for power transmission outputted from power transmitter 403 are different frequencies. Further, a configuration without power transmitter 403 may be allowed when sufficient power supply is available from data signals transmitting via a human body as a transmission line at the receiver side of cassette type FPD 2.

Carrier generator 412 generates a carrier wave to supply power for cassette type FPD 2.

BPF 413 removes noise signals (harmonic waves) from carrier inputted from carrier generator 412 to select a signal having only a needed frequency and outputs to AMP 414.

AMP 414 amplifies the transmitted signal to tuning circuit 415.

Tuning circuit 415 containing a tuning circuit selects only a signal having a needed frequency as a filter for outputting signal having a needed frequency. And also tuning circuit 415 has an effect on matching the impedance of tuning circuit to the impedance of air space as a transmission line and effectively outputs the signal. The output terminal of tuning circuit 415 is connected to transmission electrode 38 of wearable apparatus 3.

The configuration of transmitter 4 in cassette type FPD 2 does not have power transmitter 403 since it is unnecessary to transmit power to wearable apparatus 3. In regard to other units in the configuration of transmitter 4 in cassette type FPD 2, description will be omitted since they are the same as the description of transmitter 4 in wearable apparatus 3. Power supply 21, memory 25 and controller 23 may replace power supply 401, memory 404 and controller 405.

Next, the functional configuration of receiver 5 in cassette type FPD 2 will be described. As shown in FIG. 5, receiver 5 contains power supply 501, signal receiver 502 including a power receiver and power receiver 503.

Receiving electrode 28c (electrode 28 in FIG. 2) is provided on the surface of cassette type FPD 2 so that electrode 28c can be in contact with a human body. GND electrode 28d is connected to ground of cassette type FPD 2. It is not necessary to provide GND electrode 28d.

Power supply 501 comprises a battery or a rechargeable battery for supplying power to each unit. Power supply 21 of cassette type FPD 2 can replace power supply 501.

Signal receiver 502 contains tuning circuit 504, AMP 505, BPF 506, carrier generator 507, demodulator 508, memory 509 and controller 510.

Tuning circuit 504 containing a resonance circuit operates for selecting a signal having a needed frequency from receiving signals inputted from receiving electrode 28c as a filter. And also tuning circuit 504 has an effect on matching the impedance of tuning circuit 504 to the impedance of a human body as a transmission line and effectively receives the signal.

AMP 505 amplifies received modulated signals and outputs to BPF 506.

BPF 506 removes noise signals (harmonic waves) which may be generated in AMP 505 from the modulated signals amplified by AMP 505 to select a modulated signal having only a needed frequency and outputs to demodulator 508.

Carrier generator 507 usually is not necessary in receiver 5, however there is a case that a carrier generator is necessary to convert a received signal to a original signal, which is depending on a modulation method applied thereto.

Demodulator 508 derives a data signal from a received modulated signal.

Memory 509 is a memory temporarily storing data being outputted from connector 511 in cassette type FPD 2. Memory 509 comprises volatile memory such as SRAM and SDRAM, etc. or a non-volatile memory such as a flash memory, etc. Memory 25 in cassette type FPD 2 may replace memory 509.

Controller 510 usually contains CPU, etc. and controls receiver 5. Controller 510 processes received signals and stores the contents of the received signals or outputs them from connector 511. Controller 23 of cassette type FPD 2 may replace controller 510.

Power receiver 503 contains tuning circuit 512 and rectifying circuit 513.

Tuning circuit 512 contains a tuning circuit and works as a filter for selecting a signal having a needed frequency from electromagnetic waves received via power receiving antenna 27. And tuning circuit 512 matches the impedance of tuning circuit 512 to that of air space as a transmission line and can efficiently receive power.

Rectifying circuit 513 including a rectifying circuit and a smoothing circuit rectifies and smoothes signals received from power receiving antenna 27 or receiving connector 28c for obtaining a direct-current (DC) voltage and current, which can be used in receiver 5 and transmitter 4 (or a transmitter/receiver). Accordingly it is possible to conduct communications even though cassette type FPD 2 does not have a battery therein. Yet, when sufficient power can be obtained from data signals received by receiving electrode 28c via a human body as a transmission line, a configuration without power receiving antenna 27 may be allowed. In this case, since the same electrode can be used as an electrode for receiving data and supplying power, a part of the circuit of power supplying and/or an antenna become unnecessary. Consequently, it becomes possible to minimize the size of an apparatus and save cost of the apparatus.

Power receiving antenna 27 is effective when power supply from receiving electrode 28c is little and makes it possible to obtain power from another route apart from a data signal via a human body. Power receiving antenna 27 and power transmitting antenna 38 in transmitter 4 are not in contact with human body. Consequently, it is possible to supply power via air space same as normal radio communications. Since a data signal is not superposed on an electromagnetic wave for supplying power, there is no connection with data leakage.

The configuration of receiver 5 of wearable apparatus 3 does not have power receiver 503 since no power supply is conducted thereto. Since the same configuration of receiver 5 in cassette type FPD 2 is used in the configuration of receiver 5 of wearable apparatus 3, description thereof will be omitted. Power supply 31, memory 36 and controller 34 in wearable apparatus 5 can replace power 501, memory 509 and controller 510.

Figure 6:
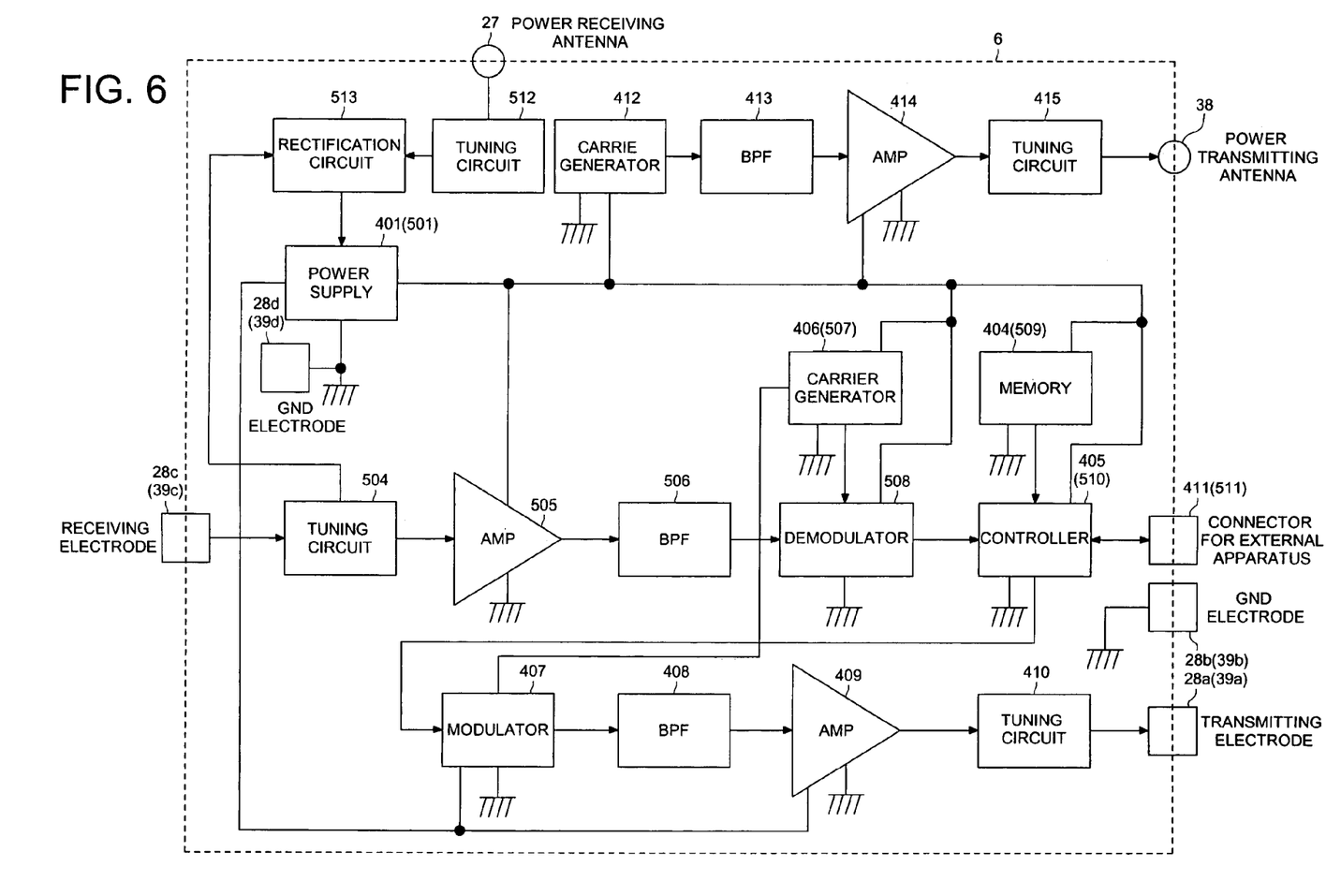
FIG. 6 is a block diagram showing the functional configuration of transmitter/receiver 6.

In the above description, transmitter 4 and receiver 5 are described as a separate device. However it may be possible to combine both transmitter 4 and receiver 5 into transmitter/receiver 6 having a transmitter function and a receiving function therein as shown in FIG. 6. As shown in FIG. 6, transmitter/receiver 6 contains power supply 401 (501), tuning circuit 504, AMP 505, BPF 506, carrier generator 406 (507), demodulator 508, memory 404 (509), controller 405 (510), modulator 407, BPF 408, AMP 409, tuning circuit 410, modulator 512, rectifier 513, carrier generator 412, BPF 413, AMP 414 and tuning circuit, etc. In regard to the configuration of transmitter/receiver 6, the same codes are put on the same configuration portion and the description of each configuration portion is omitted since these configurations and function are the same as that of transmitter 4 and receiver 5. In the case of transmitter/receiver 6, the same controller or two separate controllers can be used for the transmitter and the receiver.

Next, the operation of radiographer support system 1 will be described.

Figure 7:
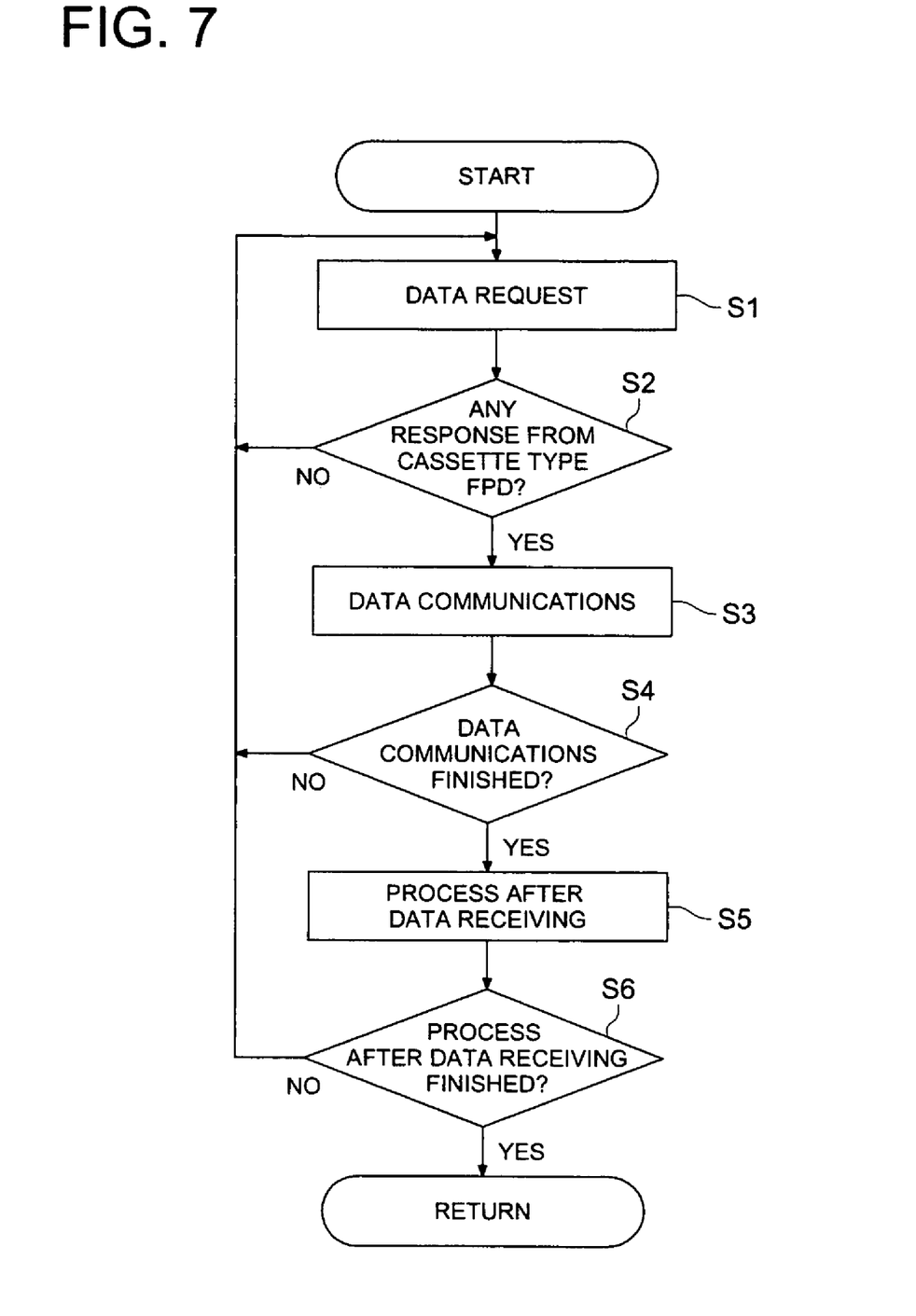
FIG. 7 is the flowchart of a communication process of radiograph related data and radiographic image data executed by radiographer support system 1.

FIG. 7 is a flow chart showing a communication process of radiograph related data and radiographic image data executed by radiographer support system 1. The radiograph related data is stored in cassette type FPD 2 in advance. The registration of the radiograph related data is conducted by PC (personal computer), etc. under the condition that cassette type FPD 2 is on a cradle connected to PC, etc. Memory 25 of cassette type FPD 2 stores radiographic image data obtained by radiographing a patient.

As shown in FIG. 7, wearable apparatus 3 issues a data request signal to cassette type FPD 2 in an every constant interval (Step 1). When no reply from cassette type FPD 2 (Step 2: NO), wearable apparatus 3 repeatedly issues the data request signal to cassette type FPD 2 (Step 1).

When the hand of a photographer wearing wearable apparatus 3 touches electrode 28 of cassette type FPD 2, namely when a reply from cassette type FPD 2 comes, a data communication between cassette type FPD 2 and wearable apparatus 3 is conducted and wearable apparatus 3 obtains radiograph related data and radiographic image data from cassette type FPD 2 (Step 3).

When finishing the data communication between cassette type FPD 2 and wearable apparatus 3 (Step 4: YES), wearable apparatus 3 issues a data receiving finish signal to cassette type FPD 2.

When finishing a data receiving finish-process (Step 6: YES), the communication process goes into a waiting condition for the next communication process of radiograph related data and radiographic image data. When the hand of a radiographer is detached from cassette type FPD 2, no response in a constant interval and the communication process goes into a communication unavailable condition (Step 4: NO, Step 6: NO), then the communication process returns to START.

Figure 8:
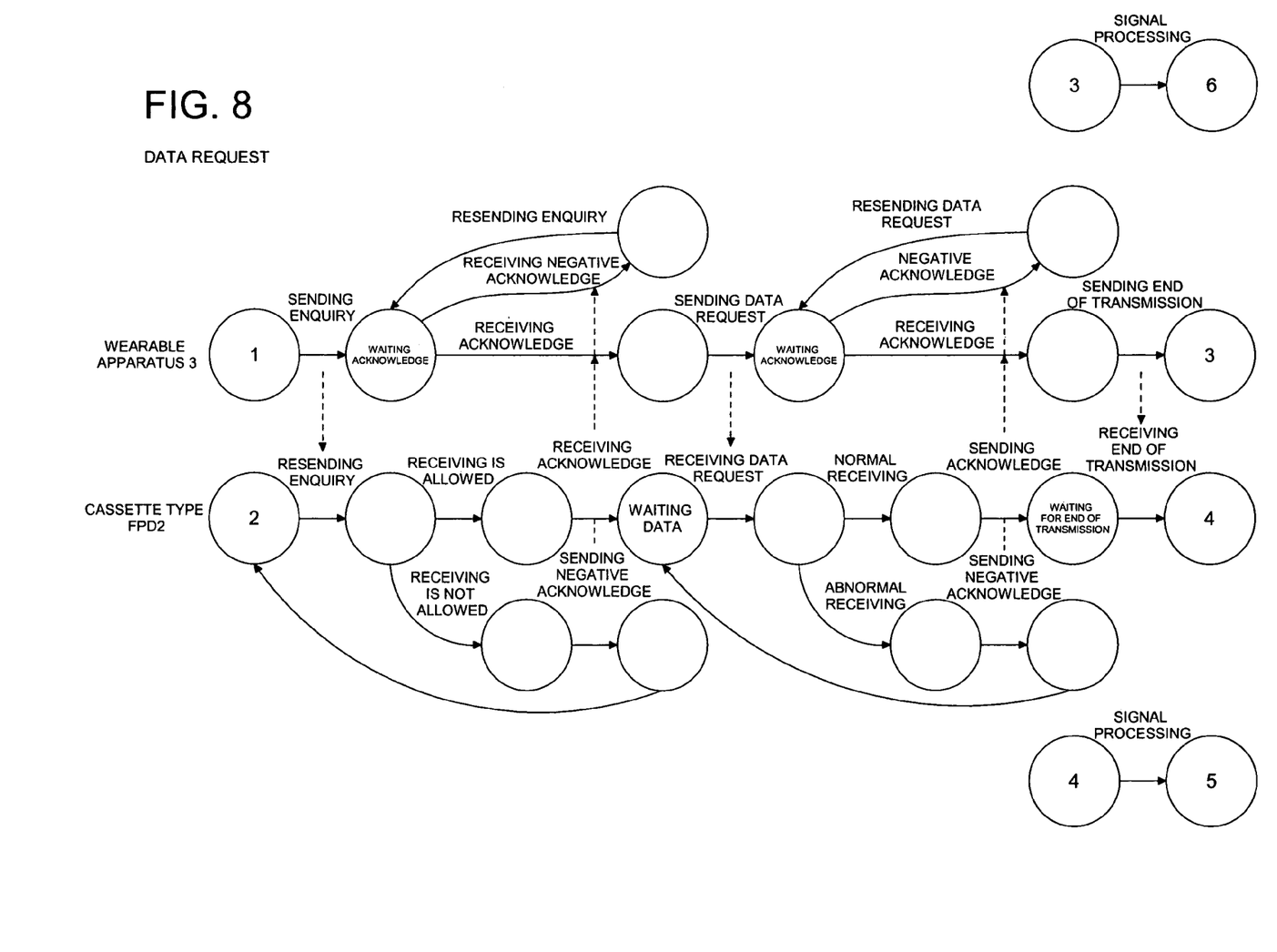
FIG. 8 is the status transition diagram of wearable apparatus 3 and cassette type FPD 2 when a data request is issued.

Various examples of each process will be described in further detail by referring status transition diagrams. FIG. 8 shows the status transition diagram of wearable apparatus 3 and cassette type FPD 2 when a data request is issued. When the data request is issued, wearable apparatus 3 issues ENQ (Enquiry or Inquiry) to cassette type FPD 2. Wearable apparatus 3 goes into a status waiting for ACK (Acknowledge).

When a radiographer wearing wearable apparatus 3 touches cassette FPD 2, wearable apparatus 3 receives ENQ from cassette FPD 2. When the status of cassette type FPD 2 is in "receiving signal available", ACK signal is sent to wearable apparatus 3 and goes into "waiting for data". When the status of cassette type FPD 2 is in "receiving signal unavailable" NAK (Negative Acknowledge) is sent and cassette type FPD 2 and goes into initial status (Status 2).

When wearable apparatus 3 receives NAK, wearable apparatus 3 reissues ENQ to cassette type FPD 2. When wearable apparatus 3 receives ACK, then wearable apparatus 3 issues a data request signal to cassette type FPD 2 and goes into "waiting for ACK".

When wearable apparatus 3 receives NAK, wearable apparatus 3 reissues a data request signal to cassette type FPD 2. When cassette type FPD 2 correctly receives the data request signal, cassette type FPD 2 issues ACK to wearable apparatus 3 and goes into "waiting for EOT (End of Transmission). When cassette type FPD 2 cannot correctly receive the data request signal, cassette type FPD 2 issues NAK to wearable apparatus 3 and goes into "waiting for data".

When wearable apparatus 3 receives NAK, wearable apparatus 3 reissues a data request signal to cassette type FPD 2. When wearable apparatus 3 receives, wearable apparatus 3 issues EOT to cassette type FPD 2 (Status 3). In this case, wearable apparatus 3 conducts the process that a data request signal has been sent (shifting to Status 6 in FIG. 9).

And, cassette type FPD 2 receives EOT (Status 4). In this case, cassette type FPD 2 conducts the process that a data request signal has been received (shifting to Status 5 in FIG. 9).

Figure 9:
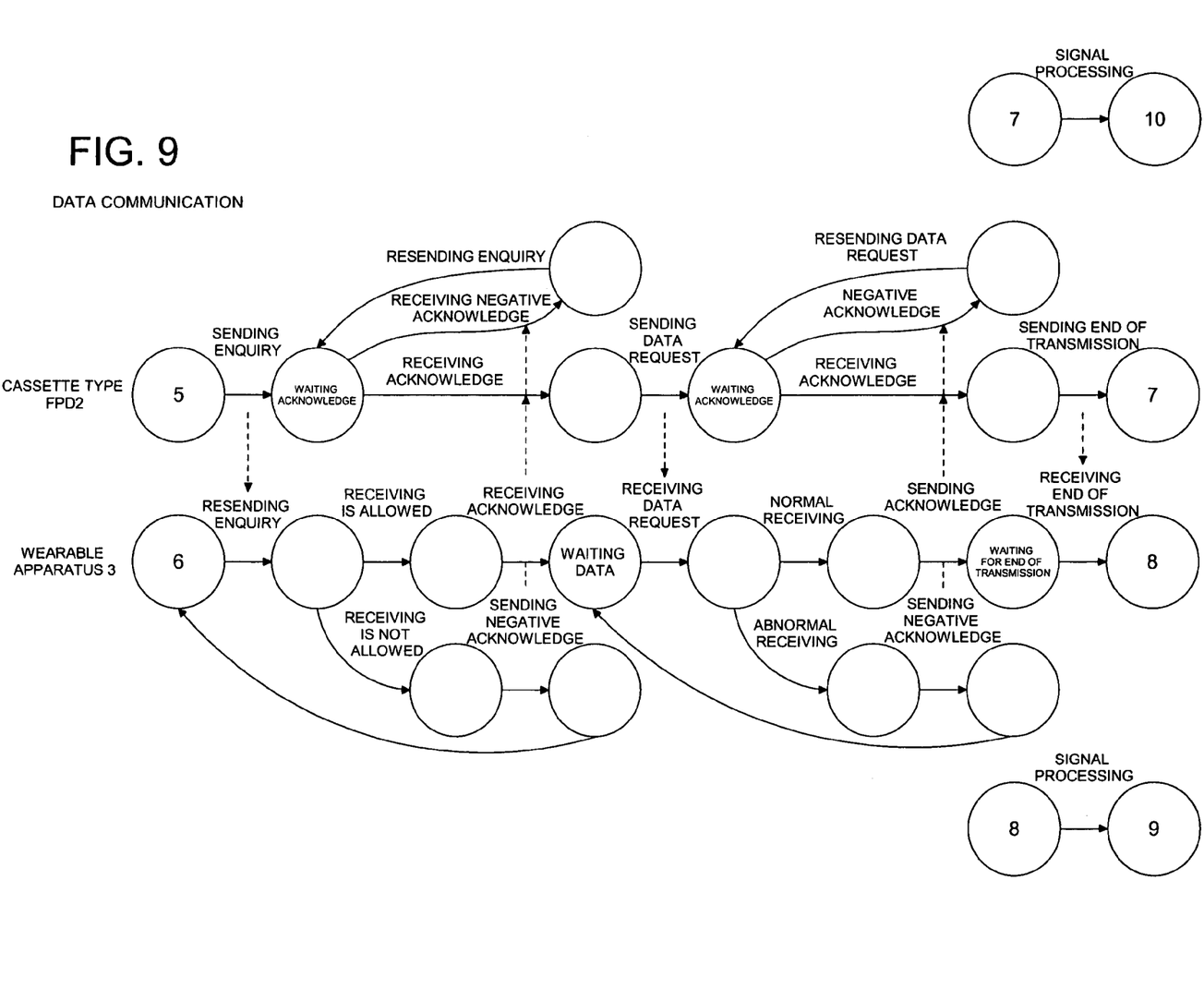
FIG. 9 is the status transition diagram of cassette type FPD 2 and wearable apparatus 3 when data communication is held.

Next, the status transition of cassette type FPD 2 and wearable apparatus 3 when data communication is held between them will be described. Firstly, as shown in FIG. 9, cassette type FPD 2 issues ENQ to wearable apparatus and goes into status "waiting for ACK".

And, wearable apparatus 3 receives ENQ. When wearable apparatus 3 is in status "receiving signal is possible", wearable apparatus 3 issues ACK to cassette type FPD 2 and goes to status "waiting for data". When wearable apparatus 3 is in status "receiving signal is impossible", wearable apparatus 3 issues NAK to cassette type FPD 2 and goes into status 6.

When cassette type FPD 2 receives NAK, cassette type FPD 2 issues ENQ to wearable apparatus 3. When cassette type FPD 2 receives ACK, cassette type FPD 2 sends data (radiograph related data and radiographic image data) to wearable apparatus 3 and goes into status "waiting for ACK".

And wearable apparatus receives the data. When wearable apparatus 3 correctly receives the data, then wearable apparatus 3 issues ACK to cassette type FPD 2 and goes into status "waiting for EOT". When wearable apparatus 3 cannot correctly receive data, wearable apparatus 3 issues NAK to cassette type FPD 2 and returns into status "waiting for data".

When cassette type FPD 2 receives NAK, cassette type FPD 2 resends data to wearable apparatus 3. When cassette type FPD 2 receives ACK, cassette type FPD 2 sends EOT to wearable apparatus 3 (Status 7). In this case, cassette type FPD 2 conducts the process that data have been sent (shifting to Status 10 in FIG. 10).

And wearable apparatus 3 receives EOT (Status 8). In this case, wearable apparatus 3 conducts the process that data have been received (shifting to Status 9 in FIG. 10).

Figure 10:
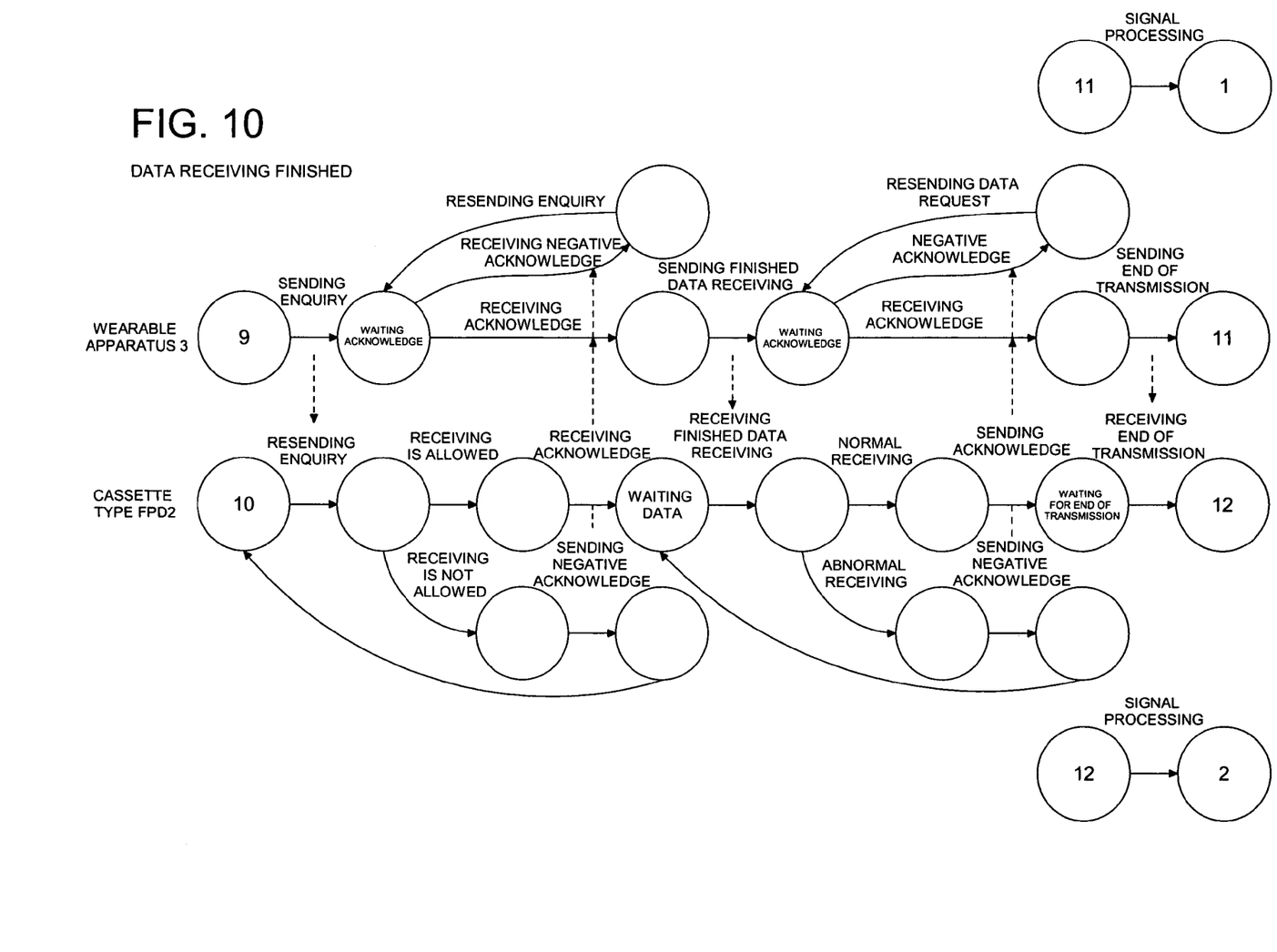
FIG. 10 is the status transition diagram of wearable apparatus 3 and cassette type FPD 2 when data receiving is finished.

FIG. 10 shows status transition of wearable apparatus 3 and cassette type FPD 2 when data receiving is finished. When data receiving is finished, firstly wearable apparatus issues ENQ to cassette type FPD 2 and wearable apparatus 3 goes into status "waiting for ACK".

And, cassette type FPD 2 receives ENQ. When cassette type FPD 2 is in status "receiving data is possible", cassette type FPD 2 issues ACK to wearable apparatus 3 and goes into status "waiting for data". When cassette type FPD 2 is in status "receiving data is impossible", then cassette type FPD 2 issues NAK to wearable apparatus 3 and returns to status 10.

When wearable apparatus 3 receives NAK, then wearable apparatus 3 reissues ENQ to cassette type FPD 2. When wearable apparatus 3 receives ACK, wearable apparatus 3 issues a signal showing that data receiving has been completed to cassette type FPD 2 and goes into status "waiting for ACK".

And cassette type FPD 2 receives the signal that data receiving has been completed. When cassette type FPD 2 has correctly received the signal that data receiving has been completed, then cassette type FPD 2 issues ACK to wearable apparatus 3 and goes into status "waiting for EOT". When cassette type FPD 2 has not correctly received a signal that data receiving has been completed, then cassette type FPD 2 issues NAK to wearable apparatus and goes into status "waiting for data".

When wearable type FPD 2 has received NAK, cassette type FPD 2 reissues the signal that data has received to wearable apparatus 3. When wearable apparatus 3 has received ACK, then wearable apparatus 3 issues EOT to cassette type FPD 2 (Status 11). In this case, wearable apparatus 3 conducts the process that data have been received (shifting to Status 1 in FIG. 8).

And cassette type FPD 2 receives EOT (Status 12). In this case, cassette type FPD 2 conducts the process that data have been received (shifting to Status 2 in FIG. 8).

Display 35 of wearable apparatus 3 displays radiograph related data and radiographic image data obtained by wearable apparatus 3. A radiographer can switch the radiograph related data and radiographic image data displayed on display 35 by operating buttons in operation unit 33. Reduced radiographic image data may be available by removing a pixel from every plural pixels obtained by wearable apparatus 3 and regenerating them. And when cassette type FPD 2 has not been used, then display 35 of wearable apparatus 3 display that cassette type FPD 2 has not been used.

According to radiographer support system 1 in EXAMPLE 1, wearable apparatus 3 can obtains radiograph related data and radiographic image data from cassette type FPD 2 via a human body as a transmission line by a human body being in touch with cassette type FPD 2 and displays information on display 35. Accordingly a radiographer can easily recognize radiograph related data such as a patient's name, a radiographic portion, radiographer's name and the data of radiographing without mistakes such as radiographing a wrong patient or a wrong radiographic portion as a object before radiographing. It is also possible to check radiographic data (including reduced image data) at the place where the radiograph is taken just after taking radiographs.

Also, radiographer support system 1 cannot be easily influenced of noise since a human body is used as a transmission line. Further, radiographer support system 1 is safer form security view point such as data leakage, etc. comparing with communication methods such as a radio LAN and a bluetooth, and can save power consumption since radiographer support system does not emit electromagnetic waves to the outside of X-ray support system.

In addition, obtaining data from cassette type FPD 2 by wearable apparatus 3 can be selected in advance according to the request from a radiographer.

EXAMPLE 2

Next, EXAMPLE 2 of the present invention will be described.

Figure 11:
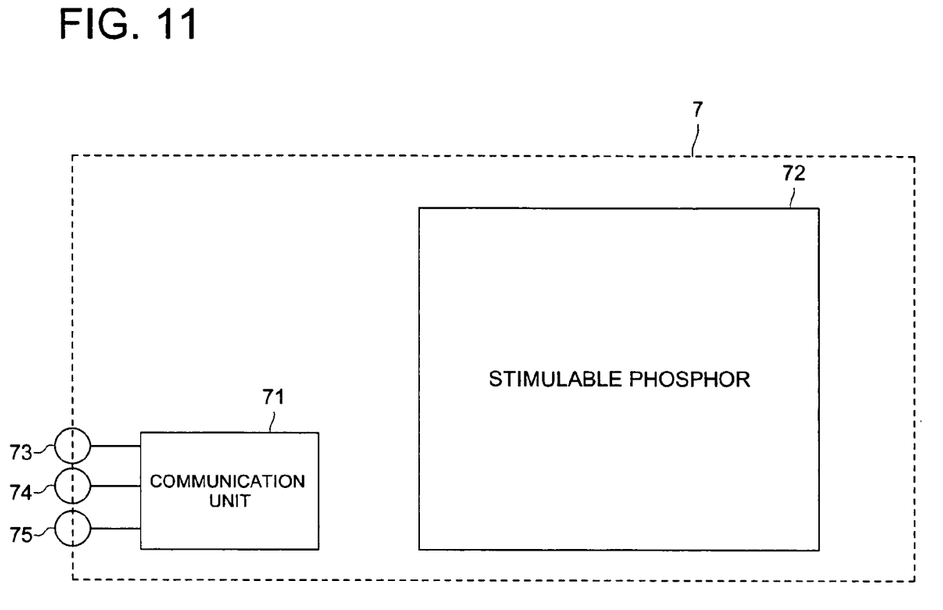
FIG. 11 shows the configuration block diagram of cassette 7 in radiographer support system in EXAMPLE 2.

In radiographer support system of EXAMPLE 1, cassette type FPD 2 is used as a recording apparatus. In a radiographer support system in EXAMPLE 2, cassette 7 is used as a recording apparatus. In regard to wearable apparatus 3, since the same wearable apparatus is used in radiographer support system 1 in EXAMPLE 1, the same code is put on the same configuration portion, and drawings and descriptions will be omitted.

FIG. 11 shows the configuration block diagram of cassette 7. Cassette 7 contains communication device 71, stimulable phosphor 72, power receiving antenna 73, electrode 74 and PC communication terminal 75 in a case. Cassette 7 is designed transportable.

Communication device 71 including CPU and memory, etc. comprises a transmitter and a receiver communicating with wearable apparatus 3 via a human body as a transmission line and a communication apparatus communicating with PC, etc. In regard to a transmitter and a receiver, since these are the same as transmitter 4 and receiver 5 shown in FIGS. 4 and 5, description will be omitted.

Stimulable phosphor 72 absorbs X-rays transmitted via a patient and holds a x-ray latent image therein. Namely, stimulable phosphor 72 is a recording media for recording a radiographic image. After radiographing, a reading apparatus obtains the radiographic image by irradiating excitation rays on to the stimulable phosphor, exciting energy absorbed in the simulable phosphor to have the simulable phosphor emit fluorescence lights and converting emitted fluorescence lights into radiographic image data via a photo-electric converter.

Power receiving antenna 73 is an interface for receiving power supplied from wearable apparatus 3, which is provided on the surface or the inside of cassette 7.

Electrode 74 provided on the case surface of cassette 7, being electrically connected with a transmitter and a receiver in communication device 71, electrode 74 is an interface to wearable apparatus 3 for data communication. Electrode 74 is provided outside of the area, where a radiographic image is generated, which is on the side surface of the case of cassette 7. Data communication is conducted when a radiographer touches electrode 74.

PC communication terminal 75 is an interface and a connector for communicating with PC by being connected with PC, etc. PC communication terminal 75 is connected with communication apparatus in communication device 71.

Radiographic related data is memorized in a memory of cassette 7 in advance. The registration of radiograph related data is conducted by inputting data from PC, etc. in the condition that cassette 7 is connected with PC, etc. In EXAMPLE 2, a memory in cassette 7 does not hold radiographic image data therein. Since radiographic image data can be obtained via a reader for reading the radiographic image data of cassette 7, data obtained from cassette 7 does not include radiographic image data.

Since the operation of radiographer support system in EXAMPLE 2 is the same as that of radiographer support system in EXAMPLE 1 except that cassette 7 is used instead of cassette type FPD 2 of radiographer support system 1 in EXAMPLE 1 and data which wearable apparatus 3 can obtain from cassette 7 is only radiograph related data, the operation of radiographer support system 1 in EXAMPLE 2 will be omitted.

According to the radiographer support system in EXAMPLE 2, wearable apparatus 3 can obtains radiograph related data via a human body as a transmission line based on a contact between a human body and cassette 7. Accordingly a radiographer can easily recognize radiograph related data such as a patient's name, a radiographic portion, radiographer's name and the data of radiographing.

Further, the description of each EXAMPLE above is preferred examples of radiographer support system of the present invention and not limited to the examples. Various modifications may be made to detailed configuration and detailed operation which configures a radiographer support system without departing from the spirit or scope of the general inventive concept.

For example, wearable apparatus 3 is described as a wristwatch type wearable apparatus. However a headphone type wearable apparatus outputting obtained information in voice, a head-mount display displaying images on a lens portion by putting on like glasses on the limb of head and a PDA (Personal Data Assistance) designed in being capable of wearing on a human body may be available. It is possible to output messages including radiograph related data and/or to output "recording apparatus is unused" in voice by using a headphone, and to display radiographic image data or radiograph related data on the screen of a display or PDA.

And in EXAMPLES described above, the data communications between a recording apparatus such as cassette type FPD 2 or cassette 7 and wearable apparatus 3 is described above. However it may applied to the data communications between plural wearable apparatuses wore on the same human body. In order to make it possible to discriminate signals used in data communications between a recording apparatus and plural wearable apparatuses, following methods such as using different frequencies, changing data code and/or recording ID (Identification) of a target apparatus into a header information are possible. According to the description above, it becomes possible to share data between plural wearable apparatuses, and information obtained by a wearable apparatus can be displayed, outputted in a voice form or stored by other wearable apparatuses.

Further, in EXAMPLES described above, data communication using a human body as a transmission line is described, however it may be possible to use a living body other than a human being.

What is claimed is:

1. A radiographer support system comprising:
    a storage apparatus provided in a case including:
        a recoding medium for recording radiographic image data;
        a recording device for recording radiograph related data of the radiographic image data;
        a first communication device electrically connected to the recording device for data communication; and
        a first electrode electrically connected to the first communication device and capable of being in contact with a human body, and
    a wearable apparatus including:
        a second communication device for communicating with the first communication device; and
        a second electrode electrically connected to the second communication device capable of being in contact with a human body;
        wherein the first communication device communicates with the second communication device to transmit the radiographic image data or the radiograph related data each other via a human body as a transmission line.

2. The radiographer support system of claim 1, wherein the radiograph related data includes one at least of a name of patient to be radiographed, a name of a portion to be radiographed, a name of radiographer or a radiographing date.

3. The radiographer support system of claim 1, wherein the wearable apparatus includes a display device for displaying the radiographic image data or the radiograph related data, or a voice outputting device for outputting the radiograph related data in a voice.

4. The radiographer support system of claim 2, wherein the wearable apparatus includes a display device for displaying the radiographic image data or the radiograph related data, or a voice outputting device for outputting the radiograph related data in a voice.

5. The radiographer support system of claim 3, wherein the wearable apparatus displays that the storage apparatus is unused for a radiograph when the storage apparatus is unused, or outputs in a voice.

6. The radiographer support system of claim 4, wherein the wearable apparatus displays or outputs in a voice that the storage apparatus is unused for a radiograph when the storage apparatus is unused, or outputs in a voice.

7. The radiographer support system of claim 1, wherein the wearable apparatus communicates with another wearable apparatus being put on a human body of the same human being via the human body as a transmission line.

8. The radiographer support system of claim 2, wherein the wearable apparatus communicates with another wearable apparatus being put on a human body of the same human being via the human body as a transmission line.

9. The radiographer support system of claim 3, wherein the wearable apparatus communicates with another wearable apparatus being put on a human body of the same human being via the human body as a transmission line.

10. The radiographer support system of claim 4, wherein the wearable apparatus communicates with another wearable apparatus being put on a human body of the same human being via the human body as a transmission line.

11. The radiographer support system of claim 5, wherein the wearable apparatus communicates with another wearable apparatus being put on a human body of the same human being via the human body as a transmission line.

12. The radiographer support system of claim 6, wherein the wearable apparatus communicates with another wearable apparatus being put on a human body of the same human being via the human body as a transmission line.

13. The radiographer support system of claim 1, wherein the storage apparatus further comprising:
    a power receiving antenna for receiving power; and
    the wearable apparatus further comprising:
    a power transmitting antenna for transmitting power to the receiving antenna, wherein
    the wearable apparatus transmits power needed for data communication to the storage apparatus either via a human body or an air space as a transmission line.

14. The radiographer support system of claim 2, wherein the storage apparatus further comprising:
    a power receiving antenna for receiving power; and
    the wearable apparatus further comprising:
    a power transmitting antenna for transmitting power to the receiving antenna, wherein
    the wearable apparatus transmits power needed for data communication to the storage apparatus either via a human body or an air space as a transmission line.

15. The radiographer support system of claim 3, wherein the storage apparatus further comprising:
    a power receiving antenna for receiving power; and
    the wearable apparatus further comprising a power transmitting antenna for transmitting power to the receiving antenna, wherein the wearable apparatus transmits power needed for data communication to the storage apparatus either via a human body or an air space as a transmission line.

16. The radiographer support system of claim 4, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

17. The radiographer support system of claim 5, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

18. The radiographer support system of claim 6, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

19. The radiographer support system of claim 7, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

20. The radiographer support system of claim 8, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

21. The radiographer support system of claim 9, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

22. The radiographer support system of claim 10, wherein
the storage apparatus further comprising:
a power receiving antenna for receiving power and the wearable apparatus further comprising:
a power transmitting antenna for transmitting power to the receiving antenna, wherein
the wearable apparatus transmits power needed for data communication to the storage apparatus either via a human body or an air space as a transmission line.

23. The radiographer support system of claim 11, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

24. The radiographer support system of claim 12, wherein
the storage apparatus further comprising:
a power receiving antenna for receiving power; and
the wearable apparatus further comprising:
a power transmitting antenna for transmitting power to the receiving antenna, wherein
the wearable apparatus transmits power needed for data communication to the storage apparatus either via a human body or an air space as a transmission line.

25. The radiographer support system as in any one of claims 1-24, wherein
the wearable apparatus is designed in a shape of a wristwatch, a head-mounted display, a headphone or a personal digital assistance.

* * * * *